United States Patent [19]
Calhoun et al.

[11] Patent Number: 6,155,971
[45] Date of Patent: Dec. 5, 2000

[54] COMPUTER IMPLEMENTED METHODS FOR REDUCING THE EFFECTS OF TINNITUS

[75] Inventors: Barbara Calhoun, Berkeley; Bret E. Peterson, Lafayette; Michael M. Merzenich, San Francisco, all of Calif.

[73] Assignee: Scientific Learning Corporation, Berkeley, Calif.

[21] Appl. No.: 09/240,066

[22] Filed: Jan. 29, 1999

[51] Int. Cl.[7] .................................................. A61M 21/00
[52] U.S. Cl. ............................................. 600/28; 600/549
[58] Field of Search ............................... 600/27, 28, 549; 128/898, 899

[56] References Cited

U.S. PATENT DOCUMENTS

| | | | |
|---|---|---|---|
| 3,855,998 | 12/1974 | Hidalgo-Briceno | 128/2.16 |
| 4,158,920 | 6/1979 | Walker | 35/22 R |
| 4,759,070 | 7/1988 | Voroba et al. | 381/60 |
| 5,024,235 | 6/1991 | Ayers | 128/732 |
| 5,092,835 | 3/1992 | Schung et al. | 600/9 |
| 5,387,104 | 2/1995 | Corder | 434/156 |
| 5,724,987 | 3/1998 | Gevins et al. | 128/731 |
| 6,019,607 | 2/2000 | Jenkins et al. | 434/116 |

FOREIGN PATENT DOCUMENTS

| | | | |
|---|---|---|---|
| 4431493 A1 | 3/1996 | Germany | A61F 11/06 |
| 2134689A | 8/1984 | United Kingdom . | |

OTHER PUBLICATIONS

Guy Bérard, M.D., Hearing Equals Behavior, 1993, pp. 80–81.

J.W. House, M.D., et al., "Putting a damper on tinnitus," *Patient Care*, pp. 82–102, 1991.

A.H. Lockwood, M.D., et al., "The functional neuroanatomy of tinnitus," *American Academy of Neurology, Neurology 50*, pp. 114–120, 1998.

Z. Seltzer, D.D.S. and M. Devor, Ph.D., "Ephaptic transmission in chronically damaged peripheral nerves," *Neurology*, vol. 29, pp. 1061–1064, 1979.

R.J. Salvi and W. A. Ahroon, "Tinnitus and Neural Activity," *Journal of Speech and Hearing Research*, vol. 26, pp. 629–632, Dec. 1983.

C.T. Sasaki, et al., "Differential [$^{14}$C]2–deoxyglucose uptake after deafferentation of the mammalian auditory pathway—a model for examining tinnitus," *Brain Research*, vol. 194, pp. 511–516, 1980.

R. Rajan, et al., "Effect of Unilateral Partial Cochlear Lesions in Adult Cats on the Representation of Lesioned and Unlesioned Cochleas in Primary Auditory Cortex," *The Journal of Comparative Neurology*, vol. 338, pp. 17–49, 1993.

(List continued on next page.)

*Primary Examiner*—Max Hindenburg
*Assistant Examiner*—Brian Szmal
*Attorney, Agent, or Firm*—Beyer Weaver & Thomas, LLP

[57] ABSTRACT

A computer-implemented method for diagnosing and/or treating tinnitus in a human subject is disclosed. The method includes generating tonal stimuli for characterizing the intensity and frequency range of the tinnitus. The method further includes generating a set of tonal stimuli used in tests comprised of tasks designed to treat the tinnitus of the human subject. The tests may be readministered at varying levels of difficulty based on the performance of the human subject. The computer-implemented method further includes providing the set of tests to the human being and receiving a response from the human being. The response from the human subject is compared to a performance threshold before potential modification of the tests. The computer-implemented method includes administration using at least two computers where at least one is local and the other is remote.

24 Claims, 9 Drawing Sheets

OTHER PUBLICATIONS

P.J. Fitzgibbons and S. Gordon–Salant, "Temporal gap resolution in listeners with high–frequency sensorineural hearing loss," *Journal of Acoustical Society of America*, vol. 81(1), pp. 133–137, Jan. 1987.

P. J. Jastreboff and C.T. Sasaki, "Salicylate–induced changes in spontaneous activity of single units in the inferior colliculus of the guinea pig," *Journal of Acoustical Society of America*, vol. 80(5), pp. 1384–1391, Nov. 1986.

B.C.J. Moore, et al., "Detection of temporal gaps in sinusoids by elderly subjects with and without hearing loss," *Journal Acoustical Society of America*, vol. 92(4), Pt. 1, pp. 1923–1932, Oct. 1992.

G.H. Recanzone, et al., "Plasticity in the Frequency Representation of Primary Auditory Cortex following Discrimination Training in Adult Owl Monkeys," *The Journal of Neuroscience*, vol. 13(1), pp. 87–103, Jan. 1993.

John S. Kauer, Ph.D., et al. "Tinnitus Aurium: Fact . . . Or Fancy," *Laryngoscope*, vol. 92, pp. 1401–1407, Dec. 1982.

P.J. Jastreboff, et al., "Neurophysical Approach to Tinnitus Patients," *The American Journal of Otology*, vol. 17, pp. 236–240, 1996.

C.K. Whittaker, M.D., "Forum," *The American Journal of Otology*, vol. 4, No. 2, p. 188, Oct. 1982.

C.K. Whittaker, M.D., "To the Editors," *The American Journal of Otology*, vol. 4, No. 3, p. 273, Jan. 1983.

S.M. Parnes, "Current concepts in the clinical management of patients with tinnitus," *Eur Arch Otorhinolaryngol*, vol. 254, pp. 406–409, 1997.

T.J. Yoo, et al., "Specific Etiologies of Tinnitus" *Tinnitus Diagnosis / Treatment*, ed. A. Shulman, et al., pp. 342–415, 1991.

B. Goldstein, "Psychophysical and Psychoacoustic Correlates of Tinnitus," *TINNITUS Diagnosis/Treatment*, ed. A. Shulman, et al., pp. 98–115, 1991.

J.A. Vernon, "Common Errors in the Use of Masking for Relief of Tinnitus," *Tinnitus Diagnos / Treatment*, ed. A. Shulman, M.D., et al., pp. 50–66, 1991.

M.P. Kilgard and M.W. Merzenich, "Cortical Map Reorganization Enabled by Nucleus Basalis Activity," *Science*, vol. 279, pp. 1714–1717, Mar. 1998.

S.L. Juliano, "Mapping the Sensory Mosaic," *Science*, vol. 279, pp. 1653–1654, Mar. 1998.

Merzenich, et al., "Temporal Processing Deficts of Language–Learning Impaired Children Ameliorated by Training," *Science*, vol. 271, pp. 77–81 (1996).

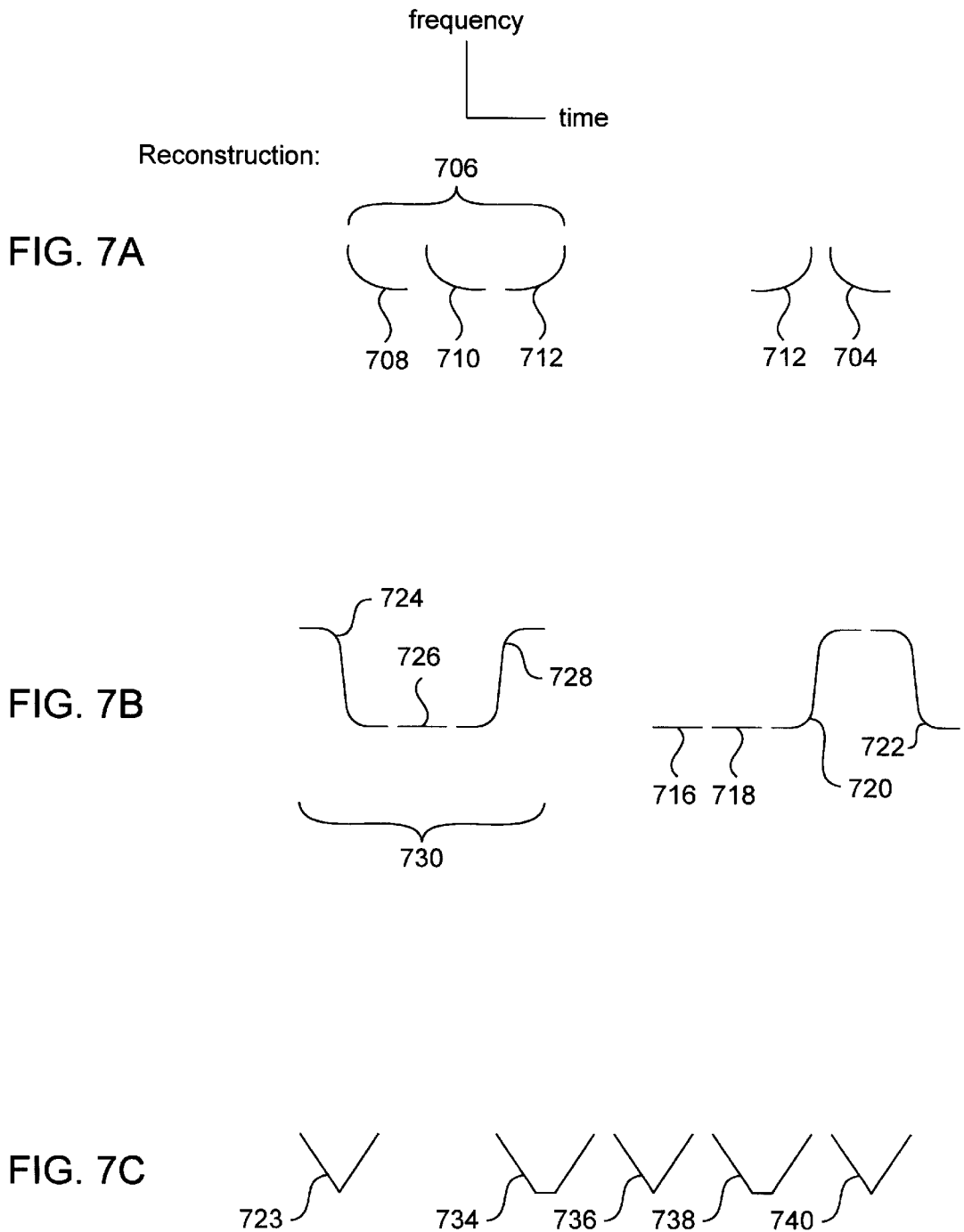

COMPUTER IMPLEMENTED METHODS FOR REDUCING THE EFFECTS OF TINNITUS

BACKGROUND OF THE INVENTION

The present invention relates generally to techniques for treating hearing disorders in people. More particularly, the present invention relates to computer implemented methods for characterizing and treating tinnitus.

Tinnitus is commonly referred to as "ringing of the ear." It is a perceived sound that cannot be attributed to an external source. One cause of tinnitus, common in hearing loss, is believed to be damage to the hair cells of the cochlea responsible for reception of sound. As an example, damage can be to the hair cells responsible for reception in the 4 kHz to 8 kHz range. As a result, sound in this frequency range may not be transformed adequately into voltage potentials that can be conducted by neurons and processed by the central auditory system. In general, tinnitus will commonly occur at the lower frequency end of the malfunctioning range, or 4 kHz in the above example. Tinnitus can vary in intensity and, as an example, may be perceived as an intensity from 5 to 10 dB, although some tinnitus sufferers have reported a higher intensity level.

Most people have experienced tinnitus, for example, after hearing a traumatically loud noise or series of loud noises over time. The effects of tinnitus have been associated with hearing loss; approximately one third of elderly people experience the problem on a regular basis. Of greater concern is the one-half to one percent of people who are considered disabled by tinnitus. For these people, tinnitus impairs their ability to lead a normal and healthy lifestyle. As a result, numerous techniques have been used to reduce the effects of tinnitus.

In the past, surgical intervention and cutting of the auditory nerve was used to reduce the effects of tinnitus. Since the malfunction was once thought to be in the cochlea, which is part of the peripheral nervous system, the surgery aimed to remove the input to the central auditory system, and perception. Despite the rather severe side effect of total hearing loss, there were many people who preferred this to suffering from the effects of tinnitus. Unfortunately, in two to four weeks, the effects of tinnitus often returned. Thus, although tinnitus may be initiated by problems in the peripheral auditory system, it is no longer thought that tinnitus is maintained solely by the peripheral nervous system.

It has been suggested that there is an increase in activity in the primary auditory cortex when a person has tinnitus. The primary auditory cortex is part of the central auditory system, which is responsible for processing the inputs of the hearing system. Another indication that the maintenance of tinnitus is in the processing portion rather than in the peripheral nervous system is that a person with tinnitus cannot adapt to the ringing in the ears the way they can to a steady ambient 5 to 10 dB sound. For example, a person with tinnitus can adapt to or shut out the sounds of a fan in the room but cannot do the same for the tinnitus. Recent treatments have focused on this ability to adapt to ambient noise.

The use of a noise masker is one current method used to treat tinnitus by continually supplying a background noise having a constant intensity and drowning out the sound of the tinnitus. This method may be used for tinnitus sufferers who have difficulty falling asleep due the discomfort of the ringing noise. It is hoped in this case that the person is more tolerant of the masker-produced noise than of the constant ringing of the tinnitus and that the person can become accustomed to the masker-noise over time. Disadvantageously, this method requires the patient to tolerate background noise over the sound of the tinnitus. Further, the person must also sacrifice hearing ability at low intensities due to the interfering background noise. And finally, the person must also be open to wearing an external hearing aid.

Another recent method for treating tinnitus is through tinnitus retraining therapy. In this therapy, a masker is used to set a a noise intensity slightly lower than the intensity needed to block the perception of the tinnitus. The goal in this case is to have the person adapt to the intitial slight difference between the tinnitus and the noise provided by the masker. When the person no longer focuses on the tinnitus with this difference, the masker noise is turned down and the person must adapt to a slightly greater difference. This gradual resetting of intensity levels and building of tolerance levels is repeated until the person does not focus on the tinnitus even without the masker.

Although the prior art techniques may, if properly administered, help the person live with the tinnitus, there are disadvantages. Both techniques described force the person to wear a hearing device. They also both rely on the presumption that the person prefers the masker-noise. Both treatments may also compromise the ability to hear low intensities. More importantly, the attempts to remedy this problem have been based on training the person to adapt to, or become more tolerant of, the tinnitus and have not focused on the abnormality in the auditory cortex that maintains the tinnitus.

In view of the foregoing, there are desired improved techniques for characterizing and treating tinnitus.

SUMMARY OF THE INVENTION

The invention relates, in one embodiment, to a computer-implemented method for characterizing tinnitus using at least two computers consisting of a remote and a local computer. The computer-implemented method includes administering evaluation tests to a human being that may characterize the current frequency or intensity of tinnitus for the human being. The performance of the human being is attained and used to modify the evaluation tests in a manner that further facilitate characterization of the tinnitus.

In another embodiment, the computer-implemented method includes a method of treating tinnitus using at least two computers consisting of a remote and a local computer. The method includes providing at least one of a set of temporal stimulus tests or spectral stimulus tests of a predetermined level of difficulty to the human being and receiving a response from the human being. The performance of the human being is ascertained and compared to a performance threshold. If the performance of the human being is better than the performance threshold, then the test or tests are increased in difficulty before readministering. Further, if the performance is not better than the performance threshold, then the test or tests are readministered at the same level of difficulty or at a decreased difficulty.

Embodiments of the present invention further relate to a computer readable medium including instructions for treating tinnitus or a method for delivering computer readable instructions for treating tinnitus. The instructions may include instructions for providing at least one of a set of temporal stimulus tests or spectral stimulus tests of a predetermined level of difficulty to the human being and receiving a response from the human being. The instructions may further include instructions for ascertaining the performance of the human being and comparison to a performance threshold. If the performance of the human being is greater than the performance threshold, then instructions are provided for increasing the difficulty of the test or tests before readministering. Further, if the performance is not greater than the performance threshold, then instructions are provided for readministering the test or tests at the same level of difficulty or at a decreased difficulty.

These and other features of the present invention will be described in more detail below in the detailed description of the invention and in conjunction with the following figures.

BRIEF DESCRIPTION OF THE DRAWINGS

The present invention is illustrated by way of example, and not by way of limitation, in the figures of the accompanying drawings in which:

FIG. 7a illustrates, in accordance with one aspect of the present invention, an exemplary reconstruction task, which is administered to the test subject during a test based on temporal variation.

FIG. 7b illustrates, in accordance with one aspect of the present invention, an exemplary reconstruction task, which is administered to the test subject during a test based on temporal variation.

FIG. 7c illustrates, in accordance with one aspect of the present invention, an exemplary recognition task, which is administered to the test subject during a test based on temporal variation.

DETAILED DESCRIPTION OF THE PREFERRED EMBODIMENTS

The present invention will now be described in detail with reference to a few preferred embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps and/or structures have not been described in detail in order to not unnecessarily obscure the present invention.

In accordance with one aspect of the present invention, there are provided computer-implemented methods using at least a remote computer and a local computer for characterizing and treating tinnitus. It has been found that the genesis of tinnitus may be attributed to abnormal transmission between the input hair cells of the ear and processing by the primary auditory cortex. By administering computer implemented exercises designed to help the auditory system process sounds in an efficient manner, and having the person respond under conditions of gradually increasing difficulty, abnormal processing of sound may be improved. The treatment is flexibly designed and comprises tests whose difficulty may vary based on the most recent characterization of the tinnitus.

Figure 1:
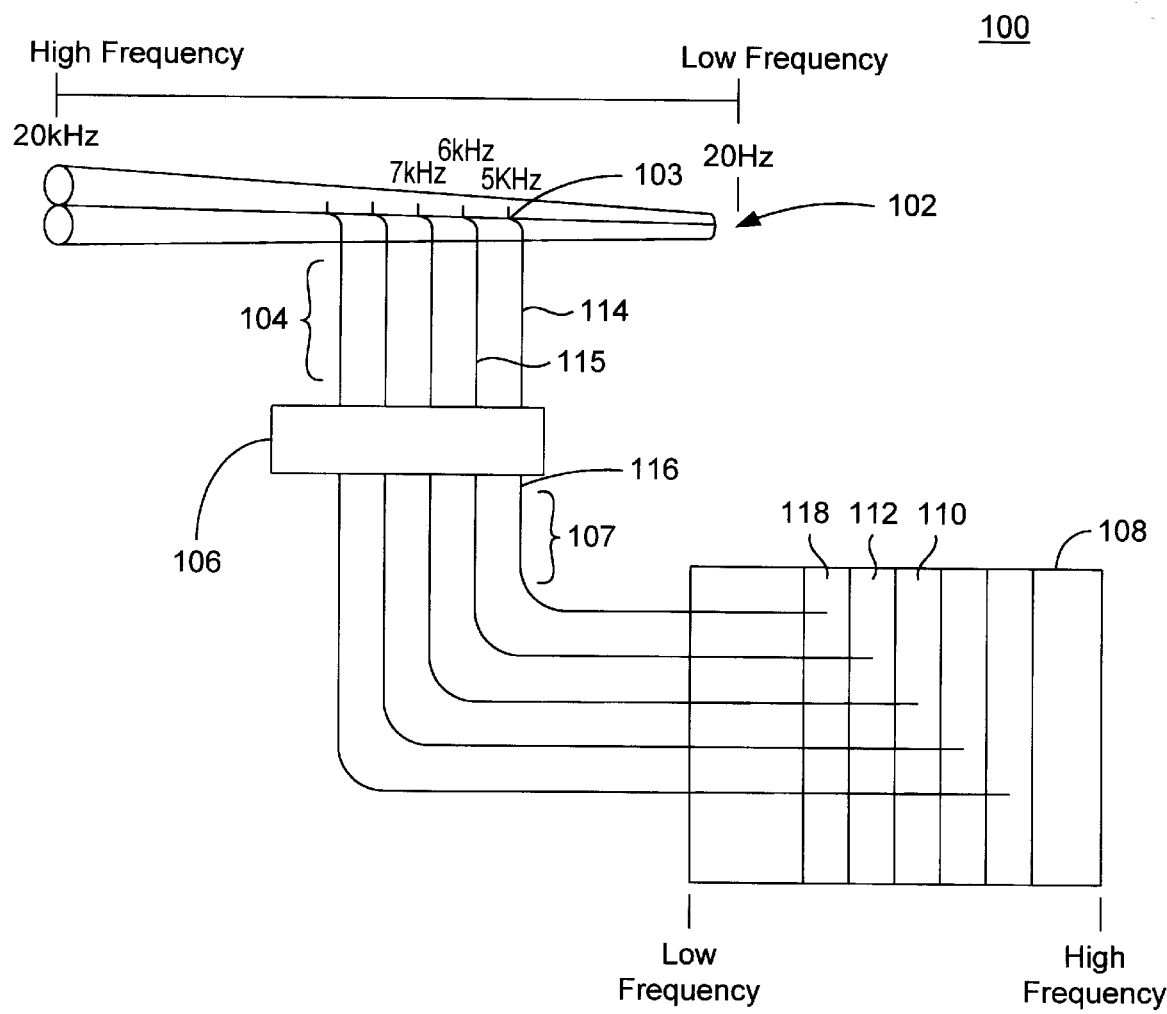
FIG. 1 illustrates a simplified version of a normal human auditory system.

To facilitate discussion, FIG. 1 illustrates a simplified representation of a normal auditory system 100. A cochlea 102 contains a plurality of hair cells 103. Hair cells 103 are responsible for transforming the energy from incoming sound waves into signals for transmission by auditory nerve fibers 104. Hair cells 103 are responsible for the reception of sound at a specific frequency. In this manner, hair cells 103 of cochlea 102 collectively span the entire range of human hearing from 20 Hz to 20 kHz. In general, one hair cell is not limited to one auditory nerve fiber as one auditory nerve fiber may combine with a plurality of hair cells, and conversely, one hair cell may combine with a plurality of auditory nerve fibers.

Broadly speaking, auditory nerve fibers 104 are responsible for transmitting signals from hair cells 103 of the cochlea 102 through a break 106. Break 106 corresponds to the parts of the auditory system between the cochlea and the primary auditory cortex that are not particularly relevant to the present discussion and thus are not shown.

The signals are carried through several nuclei (included in 106). Finally, they are transmitted by thalamocortical connections 107 to the primary auditory cortex. The above representation of the auditory system is highly simplified; additional information can be obtained by reviewing a reference entitled "An Introduction to the Physiology of Hearing" by J. D. Pickles, San Diego Acedemic Press, London, 1988. A temporal group of hair cells may refer to a group of hair cells responsive to the same frequency. Thus, a temporal group of hair cells in cochlea 102 may be mapped to by auditory nerves 104 and transmission nerves to a corresponding temporal region of primary auditory cortex 108.

To illustrate the case where a sound is processed in a normal auditory system 100, a 5 kHz sound example will be used. A group of hair cells 103 corresponding to the 5 kHz region is capable of transmitting a signal to auditory nerve fibers 114, which also correspond to 5 kHz. The signal will progress through the auditory system to thalamocortical connections 116, correspondeing to 5 kHz, to reach a region 118 of primary auditory cortex 108, which also corresponds to 5 kHz. The result will be a change in activity for a number of the neurons of region 118. When the signal sent from a hair cell maps to a specific region in the primary auditory cortex, it is said to innervate that region.

As mentioned earlier, hair cells 103 of cochlea 102 collectively cover the entire human hearing range. In general there is a tonotopic arrangement in cochlea 102 from high frequency to low frequency as illustrated in FIG. 1. Likewise, there also may be a tonotopic arrangement in primary auditory cortex 108 from high frequency to low frequency. Similarly, the auditory nerve and thalamocortical connections may be in a tonotopically arranged.

A number of hair cells 103 corresponding to 5 kHz may transmit signals to auditory nerve fibers 114, through thalamocortical connections 116 to region 118 of primary auditory cortex 108 that corresponds to 5 kHz. A threshold for perception of sound at a given frequency may be defined as the required signal level supplied by neurons of the primary auditory cortex for sound to be perceived. It is believed that when the synchronous activity of signals of the neurons in region 118, which occurs as a result of the transmission from hair cells 103, is large enough such that it meets the threshold for perception of sound, then a sound will be perceived that corresponds to the frequency of region 118. However, the threshold for perception of sound may vary for different people and may vary for a person over given frequencies.

It should be noted that hair cells 103 of cochlea 102 are continually influenced by the Brownian motion, or random motion of the fluid around the cells. Accordingly, the signal from one hair cell of hair cells 103 may be transmitted as a signal through auditory nerve fibers 104 and through thalamocortical connections 116 to primary auditory cortex 108. For a normal auditory system, the activity level produced by the neurons corresponding to the random motion of one hair cell is not enough to meet the threshold of perception of sound. In other words, for a healthy person, an individual hair cell firing alone does not innervate enough neurons to register as sound. As will be discussed in connection with FIG. 2, the situation is believed to be different for tinnitus patients.

Figure 2:
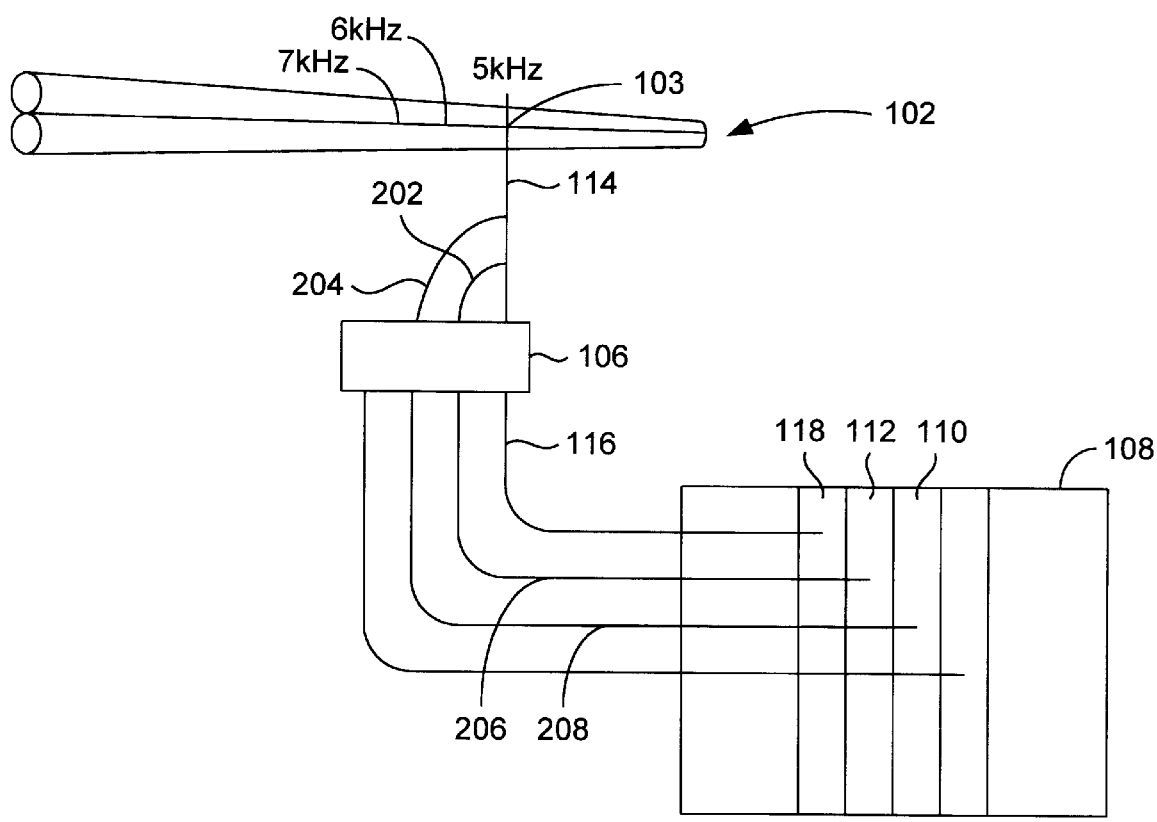
FIG. 2 illustrates a simplified version of an abnormal human auditory system.

FIG. 2 illustrates a simplified representation of an abnormal auditory system 200, which may represent an auditory system for a person with hearing loss. The hearing loss may represent tinnitus, or may represent general damage to the auditory system. Similar to the normal case, a group of hair cells 103 corresponding to 5 kHz transmit a signal through auditory nerve 114. However in this case, the damage may be represented as a loss of hair cells between 6 and 7 kHz. As a result, auditory nerve fibers 202 and 204 that correspond to the frequencies of 6 kHz and 7 kHz do not map into hair cells of corresponding frequencies. In this case, it is believed that somewhere between the hair cells and the primary auditory cortex, there is a shift such that the region of the primary auditory cortex that responded to 6–7 kHz (112) now respondes to 5 kHz.

In a manner analogous to the normal case, auditory nerve 114 still associates with thalamocortical connection 116, which in turn maps to region 118 of primary auditory cortex 108. However, the hair cells associated with kH3 (103) are now also associated with primary auditory cortex associated with 6–7 kHz (118). This increased association could occur at the level of the auditory nerve (spreading such as 202 and 204) or at any other level within the break 106. As an example of how this could occur, in the abnormal auditory system 200, a group of hair cells 103 corresponding to 5 kHz become associated with auditory nerves 114, 202 and 204. As a result, the regions of primary auditory cortex 108 that normally respond to 6 and 7 kHz now respond to an input of 5 kHz. In other words, neurons in primary auditory regions 118, 110 and 112 now all are innervated by a group of hair cells 103 that corresponds to 5 kHz.

To elaborate further, this abnormal or enlarged correlation between a group of hair cells 103 and primary auditory cortex 108 may then represent a problem for normal processing of sound. More specifically, a group of hair cells 103 that corresponds to 5 kHz may map to an enlarged region of primary auditory cortex 108 and an abnormally large number of neurons. Thus, spontaneous activity initiated by an individual hair cell in a group of hair cells 103, which under normal circumstances does not cause sound to be perceived, may in this case cause enough synchronized activity in a sufficient number of neurons in primary auditory cortex 108. In other words, random activity by hair cells 103 may result in a synchronized response in primary auditory cortex 108, which may be perceived as sound. While not wishing to be bound by theory, it is though that this perception of sound due to an increased or synchronized response in the primary auditory cortex due to random motion of a hair cell might be the genesis of tinnitus.

It should be borne in mind that the above example is illustrative and may not represent the extent or limit to which the abnormal correlation may occur. For example, the abnormal mapping may only occur from 5 to 6 kHz and may not extend to 7 kHz. It may also be possible for more than one group of hair cells to have this oversized correlation to the primary auditory cortex.

In accordance with one aspect of the invention, a computer-implemented method of treating tinnitus will be based on uncorrelating the abnormal synchronized response of primary auditory cortex 108 to a group of hair cells 103. The treatment will be based on a number of computer implemented tests that will be described later.

Figure 3:
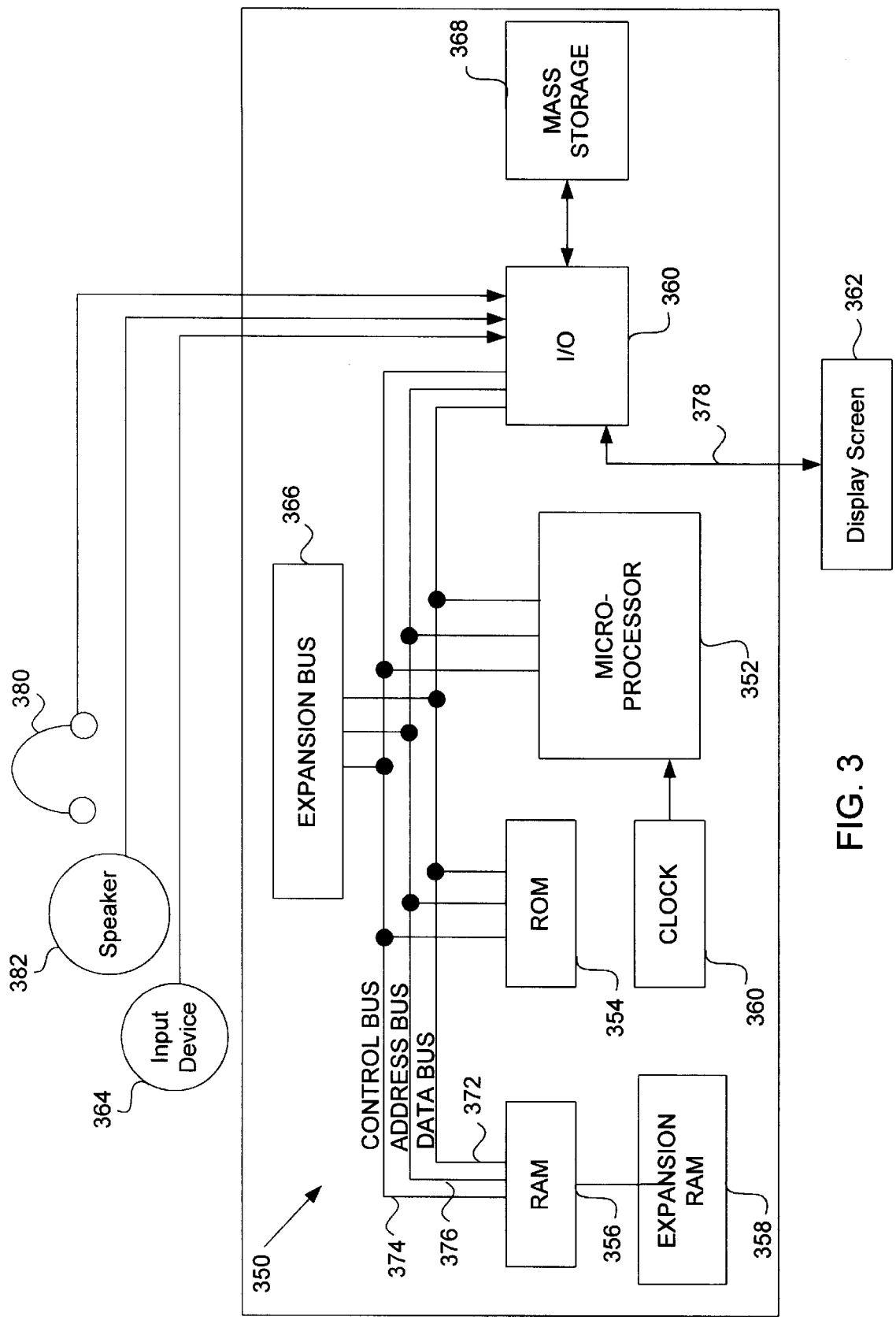
FIG. 3 shows a general purpose computer system, representing a computer suitable for implementing the present inventive tinnitus treatment method.

In general, the tinnitus treatment tests may be generated and administered using computer-implemented techniques. FIG. 3 shows a general-purpose computer system, representing a computer suitable for implementing the present inventive tinnitus treatment method. Referring to FIG. 3, a computer system 350 in accordance with the present invention includes a central processing unit (CPU) 352, read only memory (ROM) 354, random access memory (RAM) 356, expansion RAM 358, input/output (I/O) circuitry 360, display assembly 362, input device 364, and expansion bus 366. Computer system 350 may also optionally include a mass storage unit 368 such as a disk drive unit or nonvolatile memory such as flash memory and a real-time clock 360. In one embodiment, mass storage unit 368 may include units which utilize removable computer readable media, such as floppy disks, opto-magnetic media, optical media, and the like for the storage of programs and data.

CPU 352 is preferably a commercially available, single chip microprocessor such as one of the Intel X86 or Motorola 680XX family of chips, a reduced instruction set computer (RISC) chip such as the PowerPC™ microprocessor available from Motorola, Inc, or any other suitable processor. CPU 352 is coupled to ROM 354 by a data bus 372, control bus 374, and address bus 376. ROM 354 may partially contain the basic operating system for the computer system 350. CPU 352 is also connected to RAM 356 by busses 372, 374, and 376 to permit the use of RAM 356 as scratch pad memory. Expansion RAM 358 is optionally coupled to RAM 356 for use by CPU 352. CPU 352 is also coupled to the I/O circuitry 360 by data bus 372, control bus 374, and address bus 376 to permit data transfers with peripheral devices.

I/O circuitry 360 typically includes a number of latches, registers and direct memory access (DMA) controllers. The purpose of I/O circuitry 360 is to provide an interface between CPU 352 and such peripheral devices as display assembly 362, input device 364, mass storage 368, headphone 380, speaker 382, and/or any other I/O device. Display assembly 362 of computer system 350 is an output device for displaying objects and other visual representations of data.

The screen for display assembly 362 can be a device that uses a cathoderay tube (CRT), liquid crystal display (LCD), or the like, of the types commercially available from a variety of manufacturers. Input device 364 can be a keyboard, a mouse, a stylus working in cooperation with a position-sensing display, or the like. Alternatively, input device 364 can be an embedded RF digitizer activated by an "active" RF stylus. As a further alternative, input device 364 may be any type of switches capable of communicating a user response to computer system 350. Therefore, as used herein, the term input device will refer to any mechanism or device for entering data and/or pointing to a particular location on a screen of a computer display. The aforementioned input devices are available from a variety of vendors and are well known in the art.

Some type of mass storage 368 is generally considered desirable. However, mass storage 368 can be eliminated by providing a sufficient amount of RAM 356 and expansion RAM 358 to store user application programs and data. In that case, RAMs 356 and 358 can optionally be provided with a backup battery to prevent the loss of data even when computer system 350 is turned off. However, it is generally desirable to have some type of long term mass storage 368 such as a commercially available hard disk drive, nonvolatile memory such as flash memory, battery backed RAM, PC-data cards, or the like.

The acoustical signals generated by computer system 350 may be output to the tester using either headphone 380 or speaker 382. In general headphone 380 and speaker 382 may represent any suitable transducer device for generating sound waves responsive to signals from computer system 350.

In operation, computer system 350 is employed to generate temporal or spatial stimuli of the various tests at a variety of intensities. These temporal or spatial stimuli may be furnished to the test subject using either headphone 380 or speaker 382. Responses from the user may then be recorded by input device 364 and analyzed by CPU 352 to predict or ascertain hearing ability. If desired, feedback to the user may be given at various stages of the test(s) via display assembly 362.

It should be borne in mind that although computer system 350 is discussed in detail herein to facilitate discussion, the inventive tinnitus treatment technique may be practiced on a variety of suitable computer-implemented techniques. By way of example, the inventive tinnitus treatment technique disclosed herein may be implemented via a computer network, such as a local area network (LAN), wide area network (WAN) or a global computer network such as the Internet. In the latter case, the inventive tinnitus treatment technique may be implemented as downloadable computer software and data (e.g., applets). The downloadable computer software and data may be kept on one or more servers on the network, accessible by any client computer or terminal capable and authorized for such access. To facilitate testing, the downloadable computer software and data can be downloaded once and reused over and over at the client computer/terminal. Alternatively, the downloadable computer software and data can be downloaded from the remote computer to the local computer for each individual testing session via the network as needed. Network computing techniques and implementations therefor are well known in the art and are not discussed in great detail here for brevity's sake.

Characterization of the Hearing Ability

It is common for hearing impairment to affect the intensity at which a given frequency is perceived. As an illustrative example, for an elderly person with hearing loss, there can be a diminished ability to perceive sound at higher frequencies.

Figure 4:
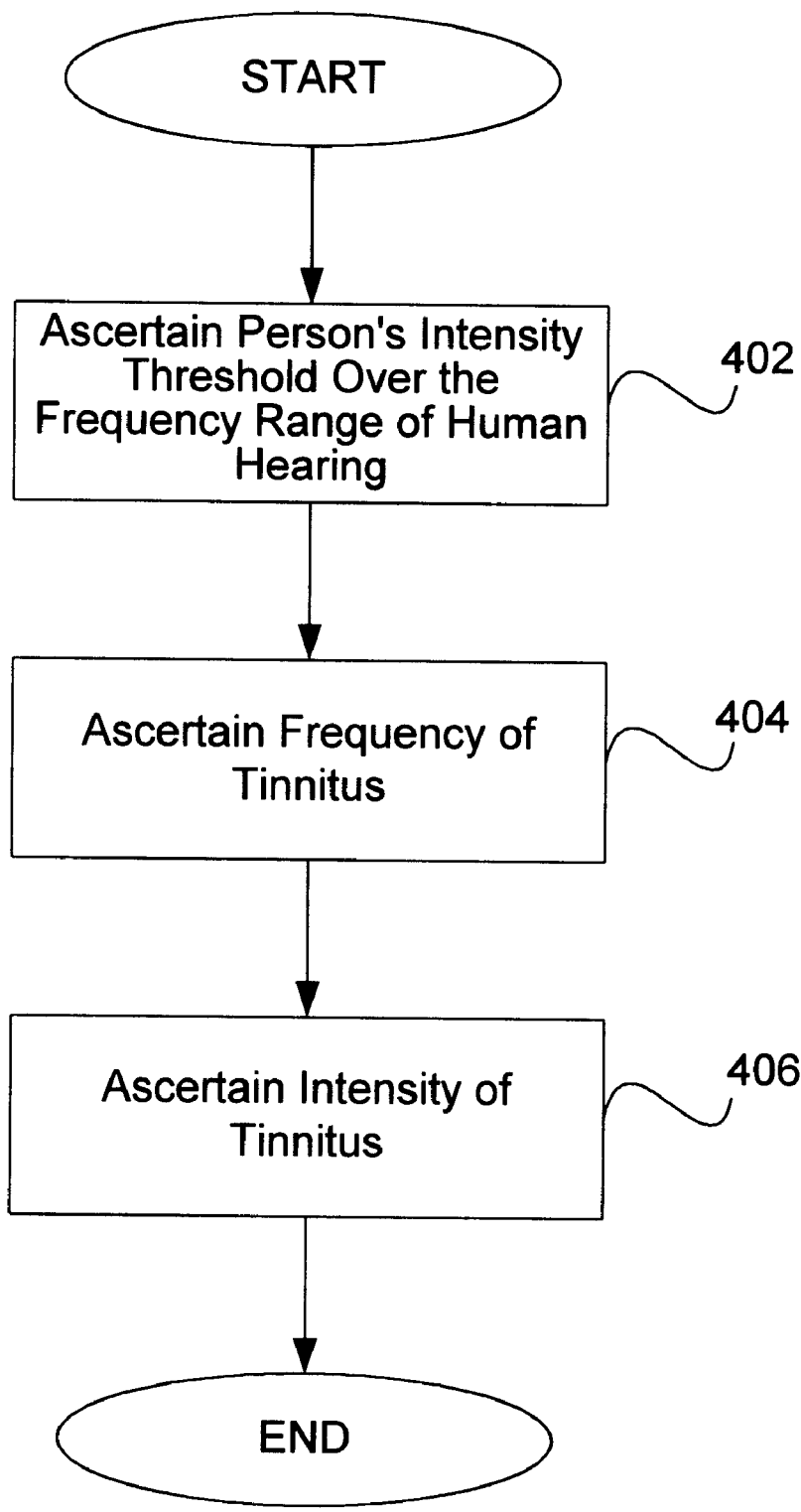
FIG. 4 illustrates, in accordance with one embodiment of the present invention, a computer-implemented method for characterizing hearing deficiency of the person.

As the first step, a person's hearing ability within the human hearing range typically needs to be ascertained. FIG. 4 illustrates, in accordance with one embodiment of the present invention, the computer-implemented method for characterizing or diagnosing tinnitus for a person.

In step 402, a series of tonal stimuli are supplied at varying parameters such as intensity or time and the person is required to respond based on perception. For example, a person may be supplied a tonal stimulus at a predetermined intensity, duration and frequency, and asked to respond if they perceive the tonal stimulus. As diagnostic testing progresses, the intensity of the tonal stimulus may decrease and the person would be required to respond. The intensity may continue to be lowered until perception of the stimulus fails. Then the computer implemented testing would readminister the tonal stimulus at increasingly stronger intensities until perception of the tone is acheived. In this manner, the intensity perception threshold at a given frequency could be established for a person. Similarly, the intensity threshold for the remaining frequency range could be established.

In step 404, the frequency range, or pitch, of the tinnitus is determined. Typically, the person is able to qualitatively distinguish the pitch of the tinnitus. The testing is implemented to determine the quantitative pitch of the tinnitus. Tonal stimuli are supplied to the person that are either higher or lower in frequency than the pitch of the tinnitus and the person responds by qualitatively assessing whether the sound is higher or lower than the tinnitus. This procedure is repeated with decreasing frequency separation between the tonal stimuli and the tinnitus until the pitch of the tinnitus is determined.

Once a frequency range has been established using the above method, a further test may be performed since it is common for a person to mistakenly equate sounds that are an octave apart. An octave increase is a doubling of the frequency. In this test, tonal stimuli in adjacent octaves are supplied and the person responds to further verify the frequency range of the tinnitus. For example, if the tinnitus has been found to begin at 5 kHz, tonal stimuli of 10 kHz, 2.5 kHz and 5 kHz are supplied, allowing the person can qualitatively differentiate which best resembles the tinnitus.

In step 406, the intensity of the tinnitus is determined. A tonal stimuli is provided at a frequency where there is no hearing loss, and the person will qualitatively respond whether the tonal stimuli or the tinnitus is stronger in intensity, i.e. louder. This procedure is repeated with decreasing intensity difference between the tonal stimuli and the tinnitus until the tinnitus intensity is determined.

Tinnitus can occasionally be a dynamic disturbance. In other words, the effects of the problem may change over time. More specifically, the frequency range at which tinnitus occurs may vary on a daily basis. The above mentioned testing can also be used to characterize this dynamic nature of the problem, further separating the proposed invention from the prior art techniques. More specifically, in accordance with one embodiment of the proposed invention, the above mentioned tests may be used to characterize the frequency range at which tinnitus occurs on a daily basis. This characterization on a daily basis may be helpful in treating the problem. It allows for the treatment parameters to be tuned to the dynamic hearing deficiency characteristics, as will be described below.

After the tinnitus has been characterized, a number of methods may be implemented to address the abnormal hearing processing problems. One method may involve a number of tests, a test being comprised of a number of tasks that the person is required to respond to. Two types of tasks that may be used to address tinnitus are spectral tasks and temporal tasks. A spectral task is one in which there is a change in the frequency component of the tonal stimuli. A temporal task is one in which the tonal stimuli vary with respect to time. Examples of temporal and spectral tasks will be further discussed in FIGS. 7 through 9.

In one embodiment of the invention, the spectral tests are designed such that the person must differentiate between stimuli with frequencies near the malfunctioning range of the hearing system. While not wishing to be bound by theory, it is believed repetitive testing may retrain portions of the primary auditory cortex to respond to frequencies other than the frequency of the tinnitus. For a person with hearing loss, the testing may also be designed such that the sections of the primary auditory cortex to be retrained are to frequencies in the range of hearing loss. As an example, for a person with tinnitus at 5 kHz and hearing loss from 5 to 7 kHz, re-training auditory region 112 in FIG. 2, which normally corresponds to 6 kHz, to a frequency other than 5 kHz may cause perception of a frequency other than 5 kHz. In this case, auditory region 112 is preferably retrained to 6 kHz, or another frequency in the deficient range of the 5 to 7 kHz range.

Figure 5:
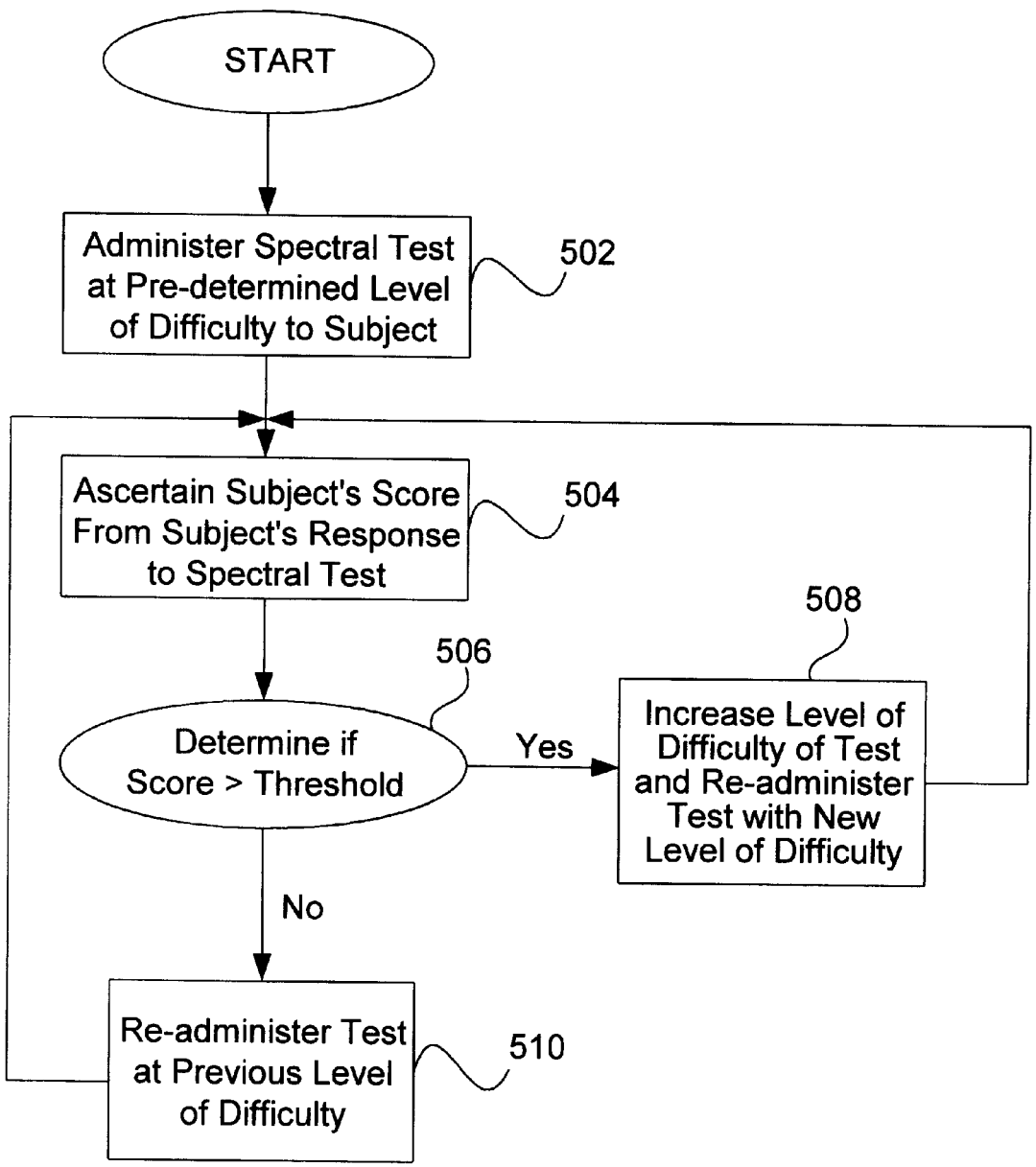
FIG. 5 illustrates, in accordance with one embodiment of the present invention, a computer-implemented method for treating tinnitus based on spectral variation of the tests.

FIG. 5 illustrates, in accordance with one embodiment of the present invention, the computer implemented method for treating a person with tinnitus using tests based on variation of spectral testing parameters. In step 502, the method generally begins with administering a test at a level of difficulty such that the person achieves a predefined success rate (preferably high) for the test. As an example, a predefined rate such as 80% may be used. In step 504, the person's score from the test is ascertained. In step 506, the score is compared to a predefined performance threshold. If the test score is above the predefined performance threshold (step 508), then the spectral test parameters are changed to increase the testing level of difficulty and the test is readministered with the new spectral parameters. Changing the test's (or exercises) spectral parameters to change the level of test difficulty may be performed by a remote computer and is further discussed in connection with FIGS. 7 to 9. The method then returns to step 504 to ascertain the score of the readministered test. If the score of the test is not above the predefined performance threshold (Step 510), then the previous test is readministered at the current level of difficulty and the method returns to step 504 to ascertain the score of the readministered test. In one embodiment, the predetermined performance threshold may be dynamic. In another embodiment, if the person fails to improve after a given number of repetitions (e.g., 2 or 3), the level of difficulty may be lowered.

Similar to the case of an enlarged frequency region that may lead to tinnitus, synchronization of signals in the temporal domain may also lead to tinnitus. For testing with the temporal tasks, it is known that a person can increase their ability to differentiate between temporal variations in sound with experience. By improving a person's temporal resolution, it may allow the reception of sound at a frequency to be converted from groups of hair cells that innervate an unproportionally large number of neurons to several hair cells that work in an uncorrelated manner. While not wishing to be bound by theory, it is believed that this repetitive testing with the temporal tasks may also unsynchronize abnormal processing that leads to tinnitus.

Figure 6:
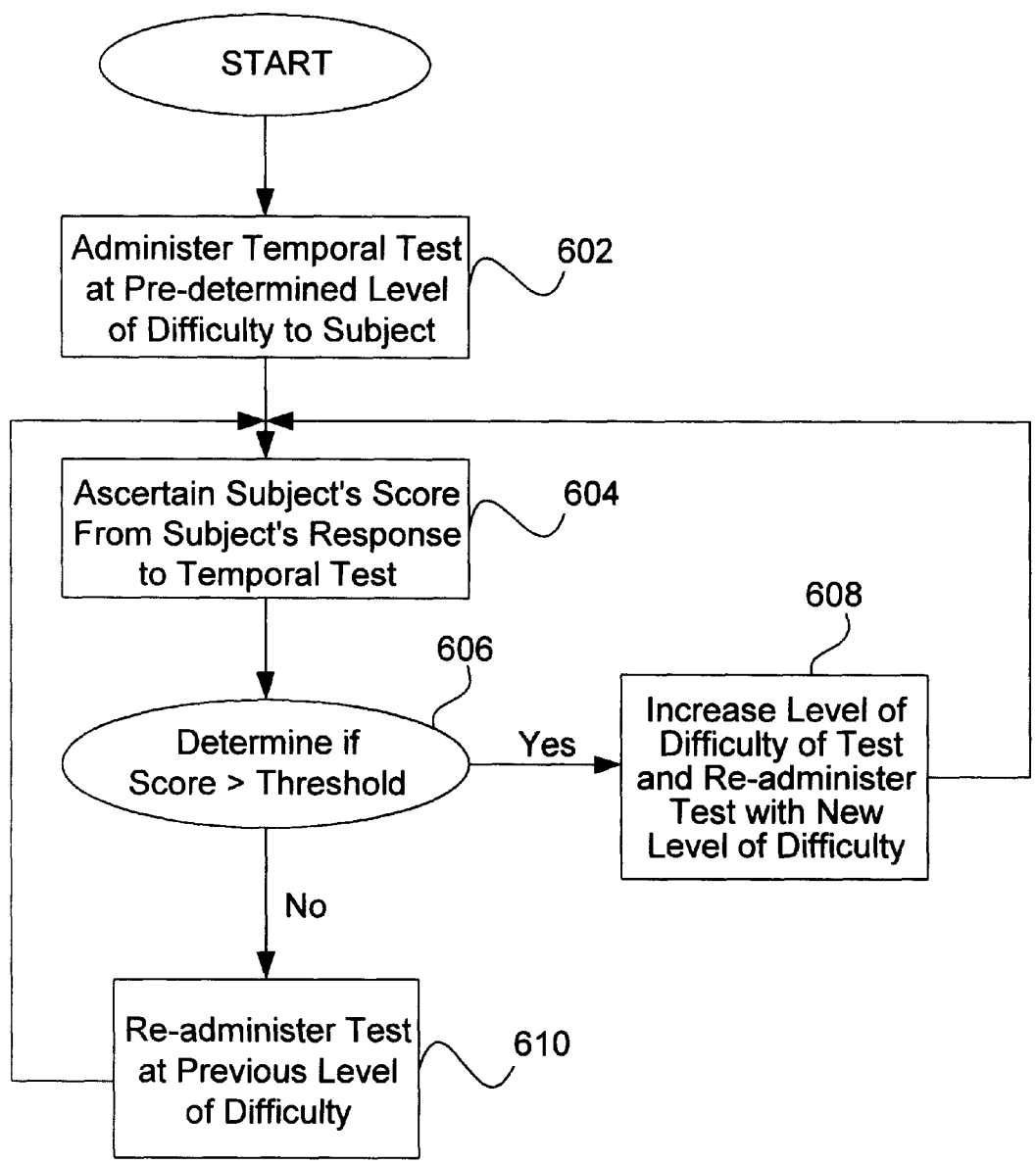
FIG. 6 illustrates, in accordance with one embodiment of the present invention, a computer-implemented method for treating tinnitus based on temporal variation of the tests.

FIG. 6 illustrates, in accordance with one embodiment of the present invention, the computer implemented method for treating a person with tinnitus using tests based on variation of spectral testing parameters. In step 602, the method generally begins with administering a temporal test at a level of difficulty such that the person achieves a predefined success rate for the temporal test (which is preferably a high success rate). As an example, a predefined rate of 80% may be used. In step 604, the person's score from the temporal test is ascertained. In step 606, the score is compared to a predefined performance threshold. If the temporal test score is above the predefined performance threshold (step 608), then the temporal testing parameters are changed to increase the level of difficulty and the test is readministered with the new temporal testing parameters. Changing the test temporal parameters to change the level of test difficulty may be performed by a remote computer and is further discussed in connection with FIGS. 7–9. The method then returns to step 604 to ascertain the score of the readministered test. If the score of the temporal test is not above the predefined performance threshold (Step 610), then the temporal test is readministered at the previous level of difficulty and the method returns to step 604 to ascertain the score of the readministered test. In one embodiment, the predetermined performance threshold may be dynamic.

In one embodiment of the present invention, testing is preferably administered for 1 hour per day, five days per week, for six weeks. It is obvious that these rates may be varied considerably based on the needs of the person. In one application of testing, hundreds of individual tasks may be administered, although this number may change based on the duration of individual tasks and the duration of testing for the day. Nevertheless, the number of tests administered should be sufficiently high to drive changes for the deficiencies in sound processing described above. In a further embodiment of the present invention, up to two thousand sounds per daily session are administered. Task parameters may be varied or different tasks may be chosen between tests based on the previous performance of the person. For example, to increase the level of difficulty of a given test, different tasks may be used or task parameters may be changed in a manner that elicits a more difficult test. Similarly, to decrease the level of difficulty of a given test, different tasks may be used or task parameters may be changed in a manner that creates a less difficult test.

Figure 8A:
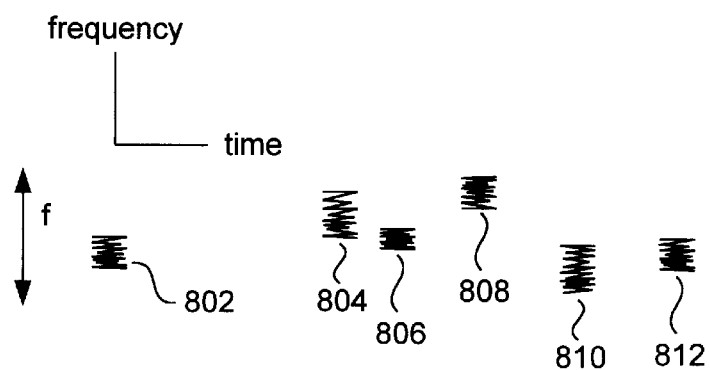
FIG. 8a illustrates, in accordance with one aspect of the present invention, an exemplary recognition task, which is administered to the test subject during a test based on spectral variation of shaped noise.
Figure 8B:
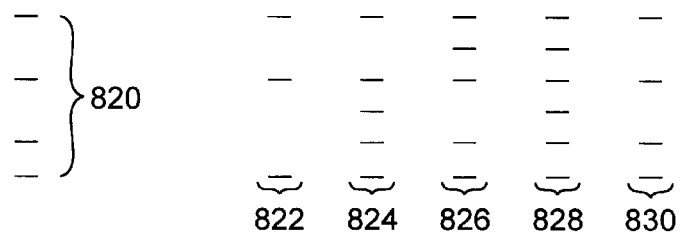
FIG. 8b illustrates, in accordance with one aspect of the present invention, an exemplary recognition task, which is administered to the test subject during a test based on spectral variation of chords.
Figure 9:
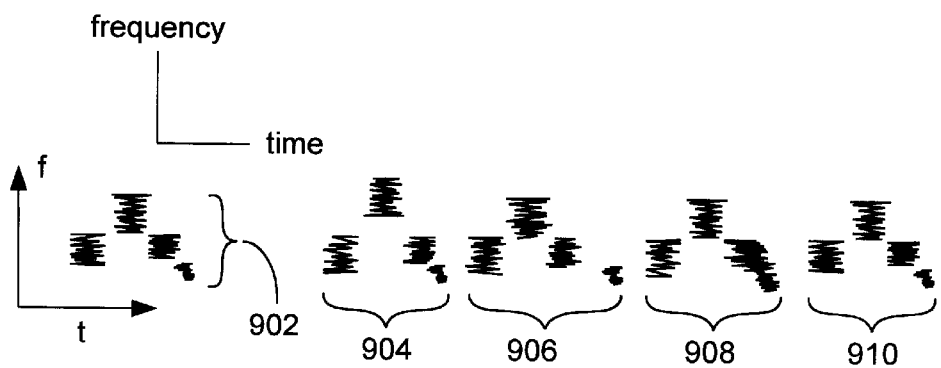
FIG. 9 illustrates, in accordance with one aspect of the present invention, an exemplary reconstruction task, which is administered to the test subject during a test based on spectral and temporal variation.

FIGS. 7 through 9 may represent individual tasks used in the sample treatments outlined in FIGS. 5 and 6. FIG. 7a illustrates, in accordance with one embodiment of the present invention, exemplary tonal stimuli, which are administered to the person in a reconstruction task utilizing temporally varying components. Examples of sound components are downward sweeping stimuli 702 in which the frequency decreases over time and upward sweeping stimuli 704 in which the frequency increases over time. A reconstruction task is a task in which the person is provided a sequence consisting of at least one sound component and must reconstruct the sequence from a set of component stimuli. As an example, sequence 706 is made up of downward sweep 708, downward sweep 710 and upward sweep 712. The task requires the person to replicate the sequence using inputs to the computer. In one embodiment of the present invention, a computer input is provided that is representative for each component. To elaborate further, the input to the computer includes a downward sweep key and an upward sweep key with which the person can reconstruct the sequence. For the case of sequence 706, the correct response would be sequentially correct input that corresponds to component tonal stimuli 704, 704 and then 702.

As mentioned above, the present invention allows for the treatment techniques to be tuned to the dynamic nature of the tinnitus problem. For example, if characterization of hearing ability is performed on a daily basis, then the results of the characterization may be used to tune the test parameters to the approximate tinnitus characteristics of that day. For example, the tonal stimuli of FIG. 7a may be tuned relative to the approximate pitch at which the tinnitus is occurring at for that day, which may be slightly different than the pitch from the previous day. In this manner, the present invention advantageously may flexibly adapt to the latest characterization, which is not done or reasonably suggested by prior techniques.

FIG. 7b illustrates, in accordance with another embodiment of the present invention, exemplary tonal stimuli, which are administered to the person in a reconstruction task also utilizing temporally varying components. In this case, the component stimuli are upward sweeps 720 and downward sweeps 722 as well as two constant tonal stimuli 716 and 718 of different lengths. Sequence 730 is a sample task sequence for reconstruction task 7b, which includes downward sweep 724, constant tonal stimulus 726 and upward sweep 728. The reconstruction task in this case requires the person to input sequence 730 from the component tonal stimuli into the computer by selecting the correct component stimuli in the correct order. In this case, the correct response is input that corresponds to downward sweep 722, constant tone 716 and upward sweep 720.

FIG. 7c illustrates, in accordance with another embodiment of the present invention, exemplary tonal stimuli, which are administered to the person in a recognition task utilizing temporally varying components. A reconstruction task is a task in which the person is provided an initial target stimulus and must identify the target stimulus from a set consisting of at least two sound components. For example, target tonal stimulus 732 is initially supplied to the person which consists of a frequency downsweep, a slight hold at constant frequency and finally a frequency upsweep. The person is then supplied with several variation tonal stimuli 734, 736, 738 and 740, which in this case, differ by the length constant frequency component. The person is then required to identify the tonal stimulus which matches the target tone. In this case, three variation tones are provided before the correct tone 740 is supplied which matches tone 732.

FIG. 8a illustrates, in accordance with another embodiment of the present invention, exemplary narrowband stimuli, which are administered to the person in a recognition task utilizing spectrally varying components. In this case, the person is provided with a plurality of shaped noises. A shaped noise is a broadband stimulus which has been filtered to within a specific frequency range (or bandwidth) around a center frequency. Target narrowband stimulus 802 is supplied prior to variations of narrowband stimuli 804, 806, 808, 810 and 812, which may differ from target narrowband stimulus 802 based on changed in the bandwidth or center frequency. In this case, four variations of narrowband stimuli are provided before the correct narrowband stimulus 812 is supplied which matches target narrowband stimulus 802.

FIG. 8b illustrates, in accordance with another embodiment of the present invention, exemplary multi-frequency stimuli, which are administered to the person in a recognition task also utilizing spectrally varying components. In this case, the multi-frequency stimuli are represented as chords. A chord may be defined as a set of tones simultaneously presented. In this case, target chord 820 is made up of four tones. Variation chords 822, 824, 826, 828 and 830 are then provided which may vary in the number and frequency of component tones. For example, in variation chord 822, a tone has been omitted in comparison to target chord 820 while in chord 824 a tone has been added. The person is then required to identify the variable chord which matches target chord 820 when it is presented. In this case, four variable chords are provided before the correct chord 830 is supplied which matches target chord 820.

FIG. 9 illustrates, in accordance with another embodiment of the present invention, exemplary tonal stimuli, which are administered to the person in a recognition task utilizing a combination of temporally and spectrally varying components. In this case, a series of shaped noises are presented sequentially in a manner in which the bandwidth, frequency center and temporal presentation of the shaped noises may vary. For example, target series 902 consists of four shaped noises. The task in this case is recognition of a variation series that matches target series 902. In this case, variation series 904 differs from target series 902 since the second shaped noise of variation series 904 is centered around a higher frequency than the second shaped noise of target series 902. Variation series 906 differs from target series 902 since the fourth shaped noise has been temporally delayed. Variation series 908 differs from target series 902 due to the addition of a shaped noise between the third and fourth shaped noise of target series 902. Thus, by changing the temporal and spectral parameters, a wide variety of tasks are possible at controllable levels of difficulty. In this case, three variable series are provided before the correct variation series 910 is supplied which matches target series 902.

It should be borne in mind that the above tests are illustrative and not meant to be restrictive with respect to what tonal stimuli and parameters are used or how they may be varied. For example, intensity may be used in the testing with tasks based on amplitude modulation where tasks vary intensity and temporal parameters. Other types of tasks that may be used in testing include tasks based on temporally and spectrally varying chords by inserting or removing a specific frequency and temporal tasks including gaps based on varying the gaps. It should also be borne in mind that tasks other than recognition and reconstruction tasks may be used as well.

As mentioned earlier, the frequency parameters of the spectral tests may be varied to accommodate the hearing abilities determined from the most recent characterization. Likewise, for the case where the person has hearing impairment, the intensity of the tests may be varied to accommodate the threshold for hearing for the person at the given frequencies of the tests being administered. More specifically, the intensity levels may be altered based on the results of the most recent characterization.

This ability to flexibly adapt the testing parameters is a novel difference of the proposed computer implemented treatment over the prior art methods. Further, the prior art techniques may be referred to as tinnitus management as they only propose to aid the individual in coping with the problem and do not attempt to improve the problem of a reorganized auditory cortex. Conversely, the proposed treatment drastically differs since it is based on improving the representation of sounds by the auditory cortex. A further distinction from the prior art is the adaptive nature of the proposed treatment which is sensitive to the dynamic nature of the hearing deficiency. For example, if the person's hearing improves over time, the computer-implemented treatment presented advantageously adapts to the changes.

By way of example, the proposed invention also covers computer readable medium that includes instructions for characterizing or treating tinnitus as described above. Yet another example of the present invention is a means for delivering computer readable instructions such as transmission, over a signal transmission medium, of signals representative of instructions for characterizing and treating tinnitus.

The methods proposed are not obvious in view of the prior art since the prior art does not suggest dynamic retraining of auditory pathways as a means of treating tinnitus. Alternatley, the prior art does not flexibly adapt the tinnitus treatment to changing levels of the tinnitus. In addition, the prior art does not suggest a treatment plan which improves hearing through correction of abnormal processing.

Another advantage of the present invention is that it may be implemented using a home computer, allowing the person the convenience to test at home without inconvenient and time consuming travel to a testing site. In one embodiment, the testing is administered over the internet where many people can be monitored by a single person at once. The proposed invention is not limited strictly to the treatment of tinnitus. Of course, other hearing disorders may be treated with the computer based methods described above. For example, hyperacusis, which is a disorder in which the person has a decreased dynamic range of hearing may be treated.

While this invention has been described in terms of several preferred embodiments, there are alterations, permutations, and equivalents which fall within the scope of this invention. By way of example, tasks based on processed speech sounds having temporal and spectral variations which may also be utilized in the testing as can tasks based on the reconstruction of chords or tone sequences. It is therefore intended that the following appended claims be interpreted as including all such alterations, permutations, and equivalents as fall within the true spirit and scope of the present invention.

What is claimed is:

1. A computer-implemented method for treating tinnitus for a human subject, said computer-implemented method comprising:

ascertaining, for the human subject, a frequency range at which said tinnitus occurs;

administering, using a computer-implemented approach, at least one set of a set of temporal stimulus-response tasks and a set of spectral stimulus-response tasks to said human subject, said at least one set being at a predetermined level of difficulty; and repeatedly performing steps a) through c) below:

a) ascertaining, using said computer-implemented approach, a performance indicator indicative of performance by said human subject on said at least one set;

b) if said performance indicator exceeds a predefined performance threshold, increasing the level of difficulty, using said computer implemented approach, of said at least one set;

c) administering, using said computer-implemented approach, said at least one set to said human subject, wherein said steps a) through c) are repeatedly administered for a number of times effective to treat said tinnitus over time.

2. The computer implemented method of claim 1 wherein said increasing includes one of using same tasks in said at least one set with more difficult parameters and using different tasks in said at least one set that are more difficult.

3. The computer implemented method of claim 1 wherein said at least one set includes tasks having varying intensity levels.

4. The computer implemented method of claim 3 wherein said at least one set includes a reconstruction task.

5. The computer implemented method of claim 3 wherein said at least one set includes a recognition task.

6. The computer implemented method of claim 1 wherein said predefined performance threshold is dynamic.

7. The computer implemented method of claim 1 further comprising the step of reporting said performance indicator to a remote computer.

8. The computer implemented method of claim 1 wherein said increasing said level of difficulty utilizes a remote computer.

9. The computer implemented method of claim 1 wherein if said performance indicator does not exceed said predefined performance threshold, then said method includes decreasing the level of difficulty of said at least one set prior to said administering.

10. The computer implemented method of claim 1 wherein said decreasing the level of difficulty further includes using the same tasks in said at least one set with less difficult parameters and using different tests in said at least one set that are less difficult.

11. The computer implemented method of claim 1 wherein said method includes a test comprised of at least 50 tasks per day.

12. The computer implemented method of claim 11 wherein said method includes testing at least five days per week.

13. A computer-implemented method, utilizing at least two computers compromising at least one local computer and at least one remote computer, for diagnosing tinnitus for a human subject, said computer-implemented method comprising:

repeatedly performing steps a) through c) below:

a) administering, using a computer-implemented approach, at least one set of a set of diagnostic tests to said human subject;

b) attaining, using said computer implemented approach, a performance response indicative of performance by said human subject on said at least one set of a set of diagnostic tests;

c) modifying, using said computer implemented approach, said at least one set of a set of diagnostic tests based on said performance response, said modifying including at least one of using same tests in said at least one set with varying parameters that further facilitate diagnosis and using different tests in said at least one set that further facilitate diagnosis.

14. The computer implemented method of claim 13 wherein said computer implemented method includes two local computers and one remote computer.

15. The computer implemented method of claim 13 wherein said set of diagnostic tests includes intensity stimulus-response tests.

16. The computer implemented method of claim 13 wherein said set of diagnostic tests includes temporal stimulus-response tests.

17. The computer implemented method of claim 13 wherein said set of diagnostic tests includes spectral stimulus-response tests.

18. The computer implemented method of claim 13 wherein said modifying of said at least one set of a set of diagnostic tests utilizes said at least one remote computer.

19. The computer implemented method of claim 13 wherein said attaining of said performance indicator utilizes said at least one remote computer.

20. A computer-implemented method, utilizing at least two computers compromising at least one local computer and at least one remote computer, for treating tinnitus for a human subject, said computer-implemented method comprising:

ascertaining, for the human subject, a frequency range at which said tinnitus occurs;

administering, using a computer-implemented approach, at least one set of a set of temporal stimulus-response tasks and a set of spectral stimulus-response tasks to said human subject, said at least one set being at a predetermined level of difficulty; and repeatedly performing steps a) through c) below:
- a) ascertaining, using said computer-implemented approach, a performance indicator indicative of performance by said human subject on said at least one set;
- b) if said performance indicator exceeds a predefined performance threshold, increasing the level of difficulty, using said computer implemented approach, of said at least one set;
- c) administering, using said computer-implemented approach, said at least one set to said human subject, wherein said steps a) through c) are repeatedly administered for a number of times effective to treat said tinnitus over time.

21. The computer implemented method of claim 20 further comprising the step of reporting said performance indicator to said at least one remote computer.

22. The computer implemented method of claim 20 wherein said increasing said level of difficulty utilizes said at least one remote computer.

23. A computer readable medium including instructions for treating tinnitus, for a human subject, said instructions comprising:

instructions for ascertaining, for the human subject, a frequency range at which said tinnitus occurs;

instructions for administering, using a computer-implemented approach, at least one set of a set of temporal stimulus-response tasks and a set of spectral stimulus-response tasks to said human subject, said at least one set being at a predetermined level of difficulty; and instructions for repeatedly performing steps a) through c) below:
- a) ascertaining, using said computer-implemented approach, a performance indicator indicative of performance by said human subject on said at least one set;
- b) if said performance indicator exceeds a predefined performance threshold, increasing the level of difficulty, using said computer implemented approach, of said at least one set;
- c) administering, using said computer-implemented approach, said at least one set to said human subject, wherein said steps a) through c) are repeatedly administered for a number of times effective to treat said tinnitus over time.

24. A computer implemented method for delivering computer readable instructions for treating tinnitus, for a human subject, said instructions comprising:

transmitting, over a signal transmission medium, signals representative of instructions for ascertaining, for the human subject, a frequency range at which said tinnitus occurs;

transmitting, over a signal transmission medium, signals representative of instructions for administering, using a computer-implemented approach, at least one set of a set of temporal stimulus-response tasks and a set of spectral stimulus-response tasks to said human subject, said at least one set being at a predetermined level of difficulty; and transmitting, over a signal transmission medium, signals representative of instructions for repeatedly performing steps a) through c) below:
- a) ascertaining, using said computer-implemented approach, a performance indicator indicative of performance by said human subject on said at least one set;
- b) if said performance indicator exceeds a predefined performance threshold, increasing the level of difficulty, using said computer implemented approach, of said at least one set;
- c) administering, using said computer-implemented approach, said at least one set to said human subject, wherein said steps a) through c) are repeatedly administered for a number of times effective to treat said tinnitus over time.

* * * * *